United States Patent [19]

Soukup et al.

[11] Patent Number: 5,330,700
[45] Date of Patent: Jul. 19, 1994

[54] POROUS ELECTRODE FOR A PACEMAKER AND METHOD OF MAKING SAME

[75] Inventors: Thomas M. Soukup, Lake Jackson, Tex.; Paul E. Kreyenhagen, Castaic, Calif.

[73] Assignee: Siemens Pacesetter, Inc., Sylmar, Calif.

[21] Appl. No.: 761,576

[22] Filed: Sep. 18, 1991

Related U.S. Application Data

[62] Division of Ser. No. 507,698, Apr. 10, 1990, Pat. No. 5,097,843.

[51] Int. Cl.$^5$ .............................. B22F 3/10; B22F 7/08
[52] U.S. Cl. .................................... 419/2; 419/8; 419/23; 419/36; 419/37; 419/53; 419/54; 427/123; 427/191; 427/436; 428/547; 428/550
[58] Field of Search ..................... 419/2, 8, 23, 36, 37, 419/53, 54; 427/123, 191, 436; 428/547, 550

[56] References Cited

U.S. PATENT DOCUMENTS

| | | | |
|---|---|---|---|
| 3,905,777 | 9/1975 | Lacroix | 29/183.5 |
| 3,981,309 | 9/1976 | Cannon | 128/419 P |
| 4,011,861 | 3/1977 | Enger | 128/419 P |
| 4,017,911 | 4/1977 | Kafpsjian et al. | 3/1.5 |
| 4,073,999 | 2/1978 | Bryan et al. | 428/311 |
| 4,156,429 | 5/1979 | Amundson | 128/419 P |
| 4,156,943 | 6/1979 | Courr | 3/1.9 |
| 4,280,514 | 7/1981 | MacGregor | 128/786 |
| 4,281,669 | 8/1981 | MacGregor | 128/784 |
| 4,309,488 | 1/1982 | Heide et al. | 428/547 |
| 4,374,669 | 2/1983 | MacGregor | 75/208 R |
| 4,408,604 | 10/1983 | Hirshorn et al. | 128/785 |
| 4,542,752 | 9/1985 | DeHaan et al. | 128/784 |
| 4,573,480 | 3/1986 | Hirschberg | 128/784 |
| 4,602,637 | 7/1986 | Elmqvist et al. | 128/419 P |
| 4,603,704 | 8/1986 | Mund et al. | 128/784 |
| 4,644,942 | 2/1987 | Sump | 623/16 |
| 4,784,159 | 11/1988 | Szilagyi | 128/784 |
| 4,784,160 | 11/1988 | Szilagyi | 128/784 |
| 4,784,161 | 11/1988 | Skalsky et al. | 128/785 |

OTHER PUBLICATIONS

Ripart et al., "Electrode-Heart Interface: Definition of the Ideal Electrode," *PACE*, vol. 8 (Mar.-Apr. 1983, Part II) pp. 410-421.

Bobyn et al., "Effect of Pore Size on the Peel Strength of Attachment of Fibrous Tissue to Porous-Surfaced Implants," *Journal of Biomedical Materials Research*, vol. 16 (1982), pp. 571-584.

*Primary Examiner*—Donald P. Walsh
*Assistant Examiner*—Daniel Jenkins
*Attorney, Agent, or Firm*—Malcolm J. Romano

[57] ABSTRACT

A porous electrode for pacemakers is comprised of a plurality of platinum globules sintered together to form a porous mass of semi-hemispherical shape at the end of a platinum electrode stem. The globules, which are themselves made by sintering together spherically-shaped particles of approximately one micron diameter, provide the globules with an irregular outer surface of high total surface area. The globules have diameters within a critical range of 40-200 microns. The large total surface area of the globules improves the sensing function of an electrode configuration of given size and surface area, while the globule diameters of 40-200 microns have been found to beneficially accommodate tissue ingrowth within the electrode. In a preferred method of making the electrode, the platinum globules, which are formed by sintering together platinum particles of much smaller size, are mixed with organic solvent and organic binder to form a paste. After application of the paste to the base of an electrode stem and pressing of the paste using a mold so as to form the paste into the desired semi-hemispherical shape, the electrode is heated to evaporate the organic solvent, and the electrode is then placed in a sintering furnace to sinter together the platinum globules and form the completed electrode.

8 Claims, 4 Drawing Sheets

POROUS ELECTRODE FOR A PACEMAKER AND METHOD OF MAKING SAME

This is a divisional of copending application(s) Ser. No. 07/507,698 filed on Apr. 10, 1990, now U.S. Pat. No. 5,097,843.

BACKGROUND OF THE INVENTION

1. Field of the Invention

The present invention relates to electrodes for implanting in body tissue, and more particularly to porous electrodes for pacemakers.

2. History of the Prior Art

It is known in the field of pacemakers and other medical devices in electrical communication with the tissue of the human body, to connect such devices to the body through porous electrodes which are in contact with the body tissue. Such porous electrodes promote fibrous ingrowth of the surrounding body tissue within the pores thereof, providing a semi-permanent attachment of the electrodes to the body tissue with the objective of reducing the size of the fibrotic capsule known to form around the electrode tip. As is well known, decreasing the size of the fibrotic capsule, especially in thickness, reduces the pacing threshold.

Typically, the electrode comprises a solid stud or stem, upon which a porous tip is formed. Porous tips of various configurations are old in the art. A totally "porous" design was achieved by encasing wire mesh in a basket screen (C.P.I. Models 4116, 4129-31). Other "porous" designs, such as Cordis Model "Encor," have only surface porosity. This is achieved by sintering microspheres only to the rigid metal substrate. With this technique, only limited tissue ingrowth (at electrode surface) is possible, leading to a "thick" fibrotic capsule about the electrode tip, creating a correspondingly high pacing threshold.

In the case of pacemaker electrodes, porous electrodes are designed-with the objective of optimizing the somewhat conflicting requirements of small stimulation surface area and at the same time large sensing surface area. For purposes of this discussion, stimulation surface area refers to the basic external dimensions of the portion of the electrode tip implanted in the body tissue. The electrode tip is usually hemispherical in shape and the stimulation surface area refers to the area A of the hemispherical profile of the tip. By the equation $J = I/A$, it is recognized that current density J is inversely proportional to the stimulation surface area A. Consequently, a relatively small stimulation surface area produces a relatively high current density. For a voltage pulse of given voltage and pulse duration provided to the heart by the pacemaker, a relatively high current density enhances the likelihood of "capture" in which successful contraction of the heart takes place.

At the same time, the sensing surface area of the electrode, which is in contact with the body tissue and fluids, should be as large as possible in order to insure proper sensing. For purposes of this discussion, sensing surface area refers to the total surface area of the porous electrode tip in contact with body tissue and fluids, including the interstitial cavities of the porous tip. Sensing relates to the ability of the pacemaker to sense electrical signals generated during depolarization. Sensing sensitivity is greatly improved by the increased sensing surface area provided by a porous electrode.

Some devices of the prior art are characterized in that electrode tips are formed by adhering together a plurality of relatively thin pieces of wire. Consequently, the surface area of the tip may be increased, not however, to the extent possible with the present invention.

Although recent attempts at the use of porous electrodes has succeeded in promoting fibrous ingrowth, the level of success falls way short of that considered acceptable. In the case of some porous electrodes, the pores may be too small to provide tissue ingrowth, which would defeat the objective of minimizing fibrotic capsule formation to obtain lower pacing thresholds. Conversely, porous electrodes in which the pores are too large results in an actual lowering of the sensing area which defeats the sensing objective.

A further problem with conventional porous electrodes resides in the insufficient total surface area of the electrodes. As previously noted, pacing requires a relatively small stimulation surface area, while sensing, in turn, dictates that the total surface area of the electrode be as large as possible. While the very presence of pores in an electrode configuration will normally provide a total surface area exposed to the interfacing tissue which is many times that of the total surface area of a nonporous electrode of like size, nevertheless such total surface area is often less than it should desirably be in order to optimize pacing and sensing.

Still further problems reside in the methods currently employed to manufacture porous electrodes. Such methods are often cumbersome or inefficient or in any event fail to optimize the desired characteristics of high total surface area for an electrode of given aggregate surface area and dimension.

SUMMARY OF THE INVENTION

Briefly stated, the present invention provides an improved porous electrode for implanting in body tissue, and an improved method of manufacturing such electrodes. An electrode in accordance with the present invention has a porous tip comprised of a plurality of globules whose dimensions fall within a critical range. With such globules joined together such as by sintering, a porous mass is established which optimizes tissue ingrowth within the electrode tip. The porous tip has a hard sponge-like shaped cross-section which facilitates vascularization therewithin.

In a preferred embodiment of the porous electrode according to the present invention, the electrode is comprised of a stem of platinum or other appropriate material which is of generally cylindrical shape and which has an electrode tip at an end thereof. The electrode tip which includes a stud extending from a disk at the end of the electrode stem has a plurality of joined together globules preferably of platinum or similar material mounted in a thick layer about the protruding stud and formed into a generally hemispherical shape. The globules have diameters within the range of 40-200 microns, and when joined together, form the porous electrode tip with the equiaxed pores in the range of 40-200 microns. This range has been found to optimize vascularization and thus tissue ingrowth into the porous electrode tip. An example of a measurement technique of pore size is described in the *Journal of Biomedical Materials Research*, Vol. 20, pgs. 1309-1333.

The pores formed within the porous electrode tip provide for excellent fibrous ingrowth by virtue of capillary action within the pores. The blood vessels which enter the pores maintain tissue life within the pores which beneficially results in the reduction of the fibrotic capsule thickness. The fibrotic capsule is formed between the electrode tip and the heart tissue to which it is in contact and acts as an impediment to energy transfer from the electrode to the heart tissue. Accordingly, a thinner fibrotic capsule gives rise to a lower voltage threshold, thereby enhancing energy transfer between the electrode and heart tissue. In other words, the thinner the fibrotic capsule or scar tissue, the higher the current density at the excitable heart tissue, which, in turn, reduces the amount of energy required to achieve the desired pacing.

Also in the preferred embodiment, the electrode tip is hemispherical in shape and the surface area of the hemispherical profile, which may be designated as the stimulation surface area, is in the range of about 1-10 square millimeters ($mm^2$). The stimulation surface area may also be defined as the total area of the periphery of the electrode tip or the peripheral surface area. The 1-10 $mm^2$ stimulation surface area provides a high current density for excellent energy transfer between the electrode tip and heart tissue. Preferably, the stimulation surface area is about 5 $mm^2$ for optimum performance.

On the other hand, it is simultaneously desirable to have as large a tip area as possible to achieve proper sensing. As has been noted, the sensing surface area relates to all the tip surface area in contact with blood and includes the surface areas of the interstitial cavities throughout the sponge-like porous mass of the electrode tip. This area may also be defined as the total interstitial surface area of the porous mass. When accounting for the total surface areas in these interstitial cavities, it is estimated that the sensing area may be orders of magnitude greater than the stimulation surface area. Thus, the present invention has successfully and uniquely solved the dilemma, which has plagued the prior art, and has achieved that which the prior art has failed to achieve. That is, an electrode tip design that satisfies tip dimension requirements which are at cross-purposes, namely, to achieve an electrode tip with relatively "small" stimulation area to create high current densities for advantageous heart tissue stimulation while having a "large" sensing area for depolarization sensing purposes.

In the preferred embodiment of the invention, each globule is provided with a relatively large total surface area by fabricating the globule from a plurality of generally spherically-shaped particles of considerably smaller size. Such particles may comprise platinum, being approximately one micron in diameter, which when sintered together form platinum globules of 40-200 microns in diameter and having a total surface area many times greater than the surface area of a smooth surfaced sphere of 40-200 microns in diameter.

Thus, at least the three following features, in combination, distinguish the present invention over the prior art devices, namely, the stimulation surface area of the electrode tip being in the range of 1-10 $mm^2$; the globule size of 40-200 microns giving rise to pore sizes of 40-200 microns for promoting capillary action and tissue ingrowth; and the globules being formed of sintered together generally spherically shaped particles having a diameter about 1 micron.

Further in accordance with the invention, porous electrodes are made by a process which begins with the provision of particles of very small size such as approximately one micron diameter. Such particles are joined together such as by sintering to produce globules of diameter within the optimum size range of 40-200 microns and at the same time having the desirable large total surface area. Such globules are then mixed with an organic solvent and an organic binder to form a paste which is then applied to the base of an electrode stem. The paste is pressed to form an electrode of desired shape. This is preferably accomplished using a mold which includes a holder having an aperture therein in which the electrode stem with paste applied thereto is placed. The mold includes a separate cap having a generally hemispherical cavity therein. With the cap pressed onto the holder of the mold, the hemispherical cavity surrounds the paste at the base end of the electrode stem and forms the paste into the desired hemispherical shape. The porous electrode as so formed is then heated in an oven to evaporate the organic solvent, following which the electrode is placed in a sintering furnace where the globules are sintered together to form the completed electrode.

BRIEF DESCRIPTION OF THE DRAWINGS

A better understanding of the invention may be had by reference to the following description, taken in conjunction with the accompanying drawings, in which.

DETAILED DESCRIPTION

Figure 1:
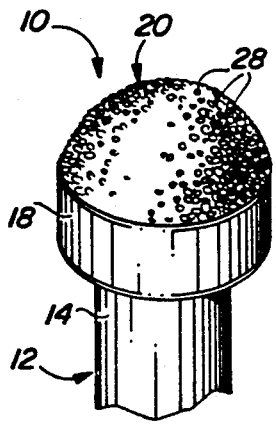
FIG. 1 is a perspective view of a porous electrode tip in accordance with the invention.

FIG. 1 depicts a porous electrode 10 in accordance with the invention. The electrode 10 includes an electrode stem 12 having a generally cylindrical body 14 which is only partly shown in FIG. 1. The cylindrical body 14 terminates in an electrode base 16 at one end thereof, which base 16 includes an enlarged disc 18 at the end of the cylindrical body 14.

The electrode 10 includes a porous tip 20 thereof which is generally of hemispherical configuration and which is formed on the disc 18 at the electrode base 16. As described in detail hereafter, the porous tip 20 is comprised of joined together generally rounded globules preferably of platinum or other appropriate material having a maximum dimension falling within a critical range so as to optimize quality tissue ingrowth within the porous tip 20 while at the same time optimizing the stimulation and sensing functions of the electrode 10.

Figure 2:
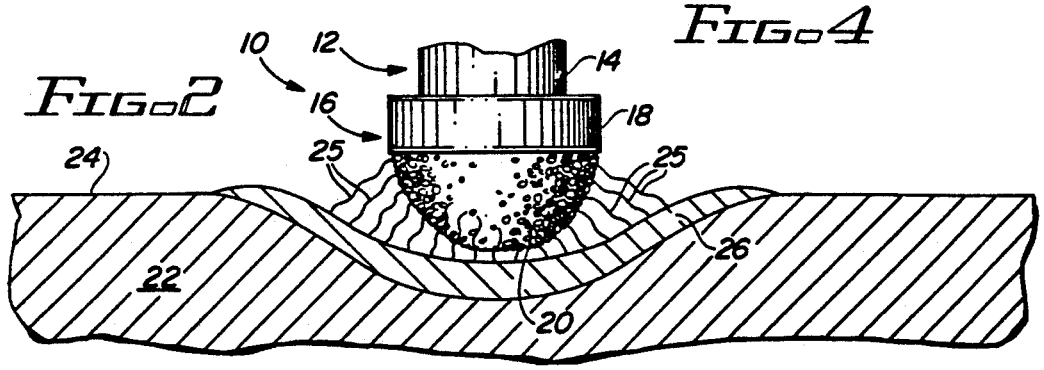
FIG. 2 is a sectional view of a mass of heart tissue with the porous electrode tip of FIG. 1 in contact with the tissue and showing the fibrotic capsule of tissue which forms around the electrode.

FIG. 2 depicts the electrode 10 in contact with the inner surface 24 of the heart tissue 22. The electrode 10 is surgically implanted in the heart so that the porous tip 20 contacts the heart tissue 22 while the electrode stem 12 with its cylindrical body 14 and its electrode base 16 remain outside of an inner surface 24 of the heart tissue 22. The electrode 10 may be surgically implanted using one of several conventional and known techniques.

Anchoring of the electrode 10 results when tissue ingrowth occurs. Tissue ingrowth within the porous tip 20 of the electrode 10 results from capillary action in the blood vessels which promote growth and sustain tissue life within the pores.

Because of the aforementioned capillary action, the living tissue within the pores gives rise to a minimal thickness fibrotic capsule 26. Otherwise, if proper ingrowth does not occur, the fibrotic capsule 26 will be relatively thicker, thereby necessitating the expenditure of much more energy required for proper pacing.

In accordance with the invention it has been observed that the pores within the porous tip 20 preferably have sizes within a limited range of values in order for proper tissue ingrowth to occur and in order for optimum electrical characteristics to result at the electrode-tissue interface. Where the porous tip 20 is formed of generally rounded globules which have been joined together, it has been found that the maximum dimension of the globules, such as their diameters, preferably falls within the range of 40-200 microns.

As best illustrated in FIG. 2, the tissue ingrowth, identified by the filaments 25, extends from the heart tissue surface 24 into the porous tip 20. The filaments 25 extend from the tissue surface 24 into the interstitial pores (as shown in FIG. 3b) throughout the porous tip 20. By means of the plurality of filaments 25, the porous tip 20 thus becomes anchored to the heart tissue 22.

Figure 3A:
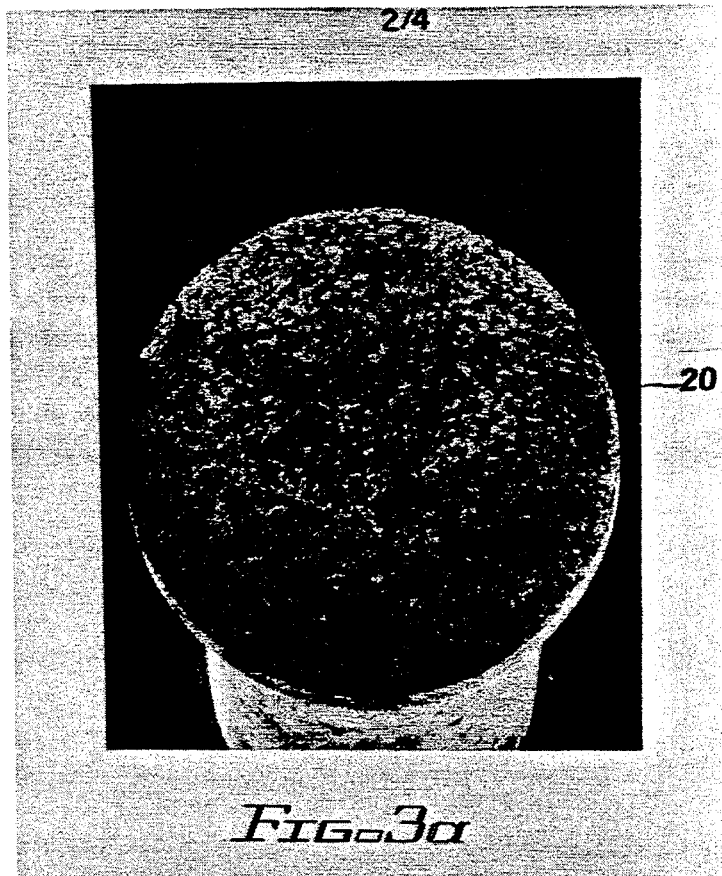
FIG. 3a is a photograph of the porous electrode tip of FIG. 1, which has been magnified many times.
Figure 3B:
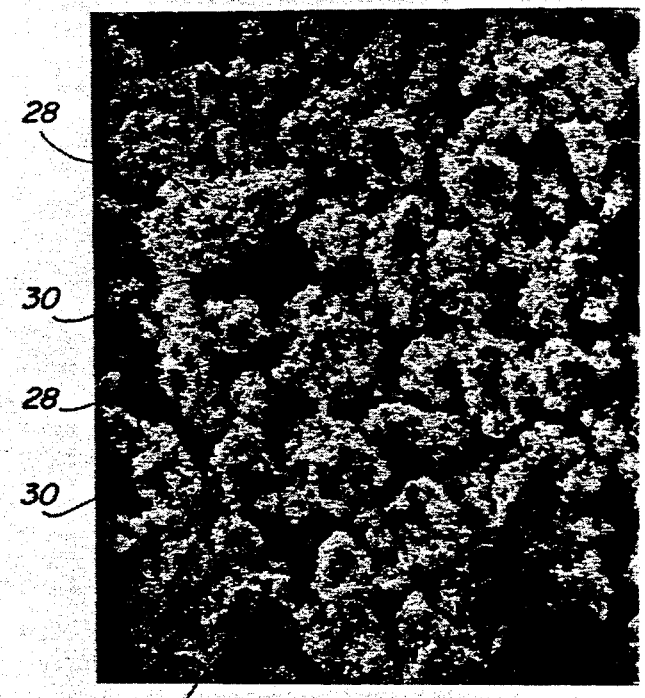
FIG. 3b is a photograph of a portion of the porous electrode tip of FIG. 3a which has been magnified many times and which illustrates several of the joined together globules that form the porous tip of the electrode.

FIG. 3a is a photograph of the porous tip 20, illustrating the hemispherical profile and the peripheral surface contour of the tip 20. As is apparent from FIG. 3a, the surface of tip 20 has a somewhat porous appearance. To better illustrate the porous nature of the porous tip 20, reference is made to FIG. 3b.

FIG. 3b is a photograph of a portion of the porous tip 20 which has been magnified many times in order to illustrate the nature of the forming globules 28 and the pores 30 (some of which are identified as the dark areas between adjacent globules) which result therebetween. The globules which preferably are made of platinum but which may also be comprised of titanium or other appropriate electrode metals have diameters in the range 40-200 microns and which have been joined together such as by sintering. As shown in FIG. 3b, the globules 28 which have been joined together form pores 30 therebetween into which desired tissue ingrowth takes place. The pores 30, as measured equiaxially, have a dimension in the range of 40-200 microns. That is, the distance between opposite facing points in a pore is between 40-200 microns.

As noted, the diameters of the globules 28 fall within the critical range of 40-200 microns in order for optimum quality tissue ingrowth to occur. Globules having diameters below the lower limit of 40 microns may eventually produce fixation of the porous tip 20 to the heart tissue, with however a resulting thicker fibrotic capsule 26 with the inherent deficiencies already noted. If the globules 28 are too large such that the diameters thereof begin to significantly exceed the 200-micron upper limit, then the sensing surface area of the electrode is undesirably decreased.

Figure 4:
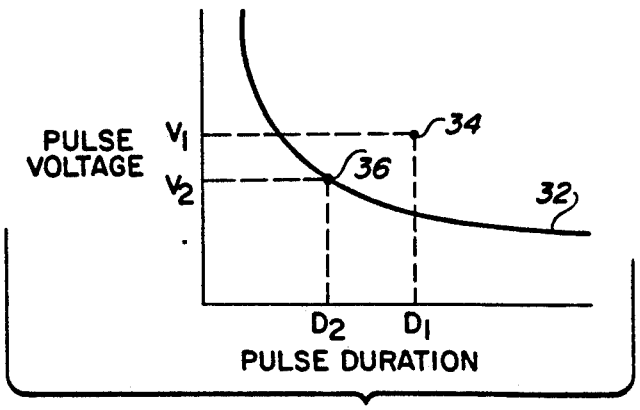
FIG. 4 depicts a curve representing the pacing characteristics of a given electrode such as the porous electrode of FIG. 1.

The manner in which pacing is accomplished using an electrode such as the porous electrode 10 may be better understood by referring to a curve 32 shown in FIG. 4. The curve 32 represents the physiological response characteristics for heart stimulation for a particular implanted electrode. The vertical axis of FIG. 4 represents pulse voltage and the horizontal axis represents pulse duration. Pulses generated by a pacemaker and transmitted to the heart via electrodes such as the electrode 10 are provided with the requisite voltage and requisite pulse duration to achieve "capture"; that is, contraction of the heart. With reference to FIG. 4, in order for "capture" to occur so that proper pacing of the heart is accomplished, the pulse voltage and duration must be at values so that the coordinates of the point defined by such values lie above the curve 32. Thus, if the pulse generated by the pacemaker has a voltage $V_1$ and a duration $D_1$, then the two values $V_1$ and $D_1$ produce a point 34. Inasmuch as the point 34 is well above the curve 32, "capture" will occur and contraction of the heart is thereby achieved. The curve 32 therefore represents the locus of points representing the corresponding combination of values of pulse voltage and duration at which "capture" will occur. Points above the curve 32 that indicate "capture" will occur, whereas points below the line indicate that capture will not occur. Thus, at a point 36 on the curve 32 which corresponds to a pulse voltage $V_2$ and a pulse duration $D_2$, capture will just begin to occur. Any reduction in the voltage $V_2$ or the pulse duration $D_2$ or both will cause the point 36 to fall below the curve 32 so that contraction of the heart does not occur.

The location of the curve 32 in FIG. 4 is a function of current density through the porous tip 20. The current density in turn is a function of the stimulation surface area of the porous tip 20. The smaller the stimulation surface area of the porous tip 20, the greater will be the current density which has the effect of moving the curve 32 toward the origin of the vertical and horizontal axes. This represents an improvement in pacing, inasmuch as "capture" will occur as a result of reduced pulse voltage or duration or both. A stimulation surface area in the range of 1-10 $mm^2$ is considered optimum for good pacing with pacemaker electrodes of the type and size described herein. With electrodes having an stimulation surface area in that range, pacemaker pulses of approximately 2.5 volts in magnitude and one millisecond in duration normally will produce contraction of the heart.

While the stimulation surface area of the porous tip 20 must be kept at a relatively small value in order to optimize pacing, the sensing surface area of the porous tip 20 is desirably made as large as possible in order to optimize sensing. In addition to providing a succession of pulses which pace the heart, heart pacemakers also monitor the responsive behavior of the heart by sensing electric signals produced by the heart during depolarization. Although the pacing pulses generated by the pacemaker may be on the order of 2.5 volts or greater, the pacemaker must be able to sense electrical signals from the heart (evoked response), which may be on the order of 0.05–0.2 millivolts.

In order for sensing to take place, the total sensing surface area of the porous tip 20 must be substantially greater than the stimulation surface area which controls pacing and which is basically defined by the external dimensions of the porous tip 20. Thus, the challenge of good lead design is to detect evoked response while being capable of proper stimulation. A sensing surface area as much as one hundred times that of the stimulation surface area may be necessary in order to achieve good sensing, but ratios of at least 5 to 1 for sensing to stimulation surface may be adequate. Porous electrodes are highly advantageous in this respect, inasmuch as the very nature of the porous configurations of such electrodes results in a large total surface area for a given aggregate surface area. The above ratios derive from a consideration of the aggregate of the surface areas of the 1 micron particles in obtaining the sensing area. To arrive at the aggregate surface area, it is considered that 50% of the sphere surface area is exposed. With the above consideration, a total "exposed" surface area or sensing area of about 500 mm$^2$, is calculated for the porous tip 20. With a preferable tip stimulation area of 5 mm$^2$, then the ratio of sensing area to stimulation area is about 100 to 1.

Figure 5A:
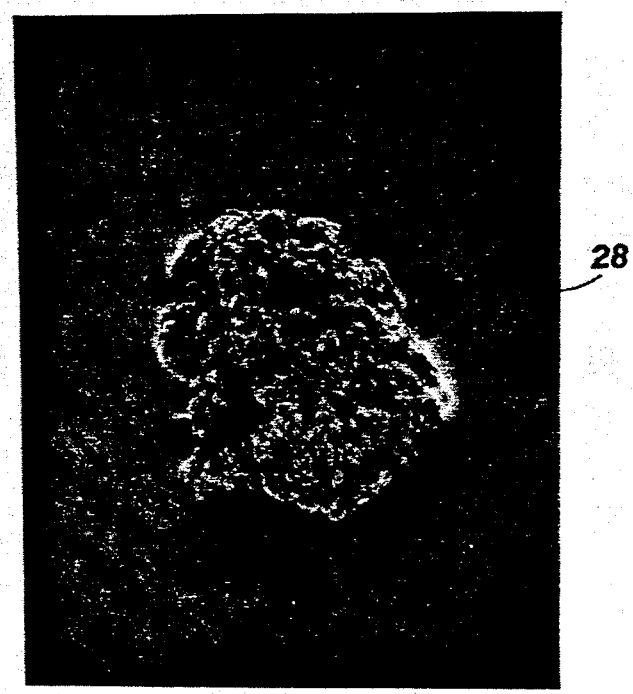
FIG. 5a is a photograph similar to that of FIG. 3b but magnified by an even greater amount so as to illustrate one of the globules in the photograph of FIG. 3 in greater detail including the highly irregular surface thereof which provides a high sensing surface area.

In accordance with the present invention the sensing surface area of the porous tip 20 is increased relative to the stimulation surface area of the porous tip 20 by virtue of the nature of the globules 28. This is accomplished by forming each of the globules 28 from a plurality of particles of considerably smaller size, which particles are joined together by sintering. This provides each of the globules 28 with a surface that is highly irregular and which therefore has a relatively large total surface area. FIG. 5a illustrates one of the globules 28 with its highly irregular outer surface and its resulting high total surface area.

In the present example, each of the globules 28 is formed from a plurality of generally spherically-shaped particles of approximately one micron diameter. The particles are formed by atomizing very small quantities of molten platinum. Such formed platinum particles 29 (shown in FIG. 5b) are then joined together by techniques such as by sintering so as to form each of the globules 28. The sintering process raises the temperature of the globules 28 to a level just above the melting point of platinum so that the globules thus are securely joined together.

It has been found that a porous tip 20 formed from globules 28 which are themselves formed from considerably smaller particles, so as to have the irregular outer surface shown in FIG. 5a, provide the porous tip 20 with a total surface area that is substantially greater than the total surface area of electrodes formed from spheres having smooth outer surfaces. This increased surface area acts to optimize the sensing of an electrode 10 of given stimulation surface area.

Figure 5B:
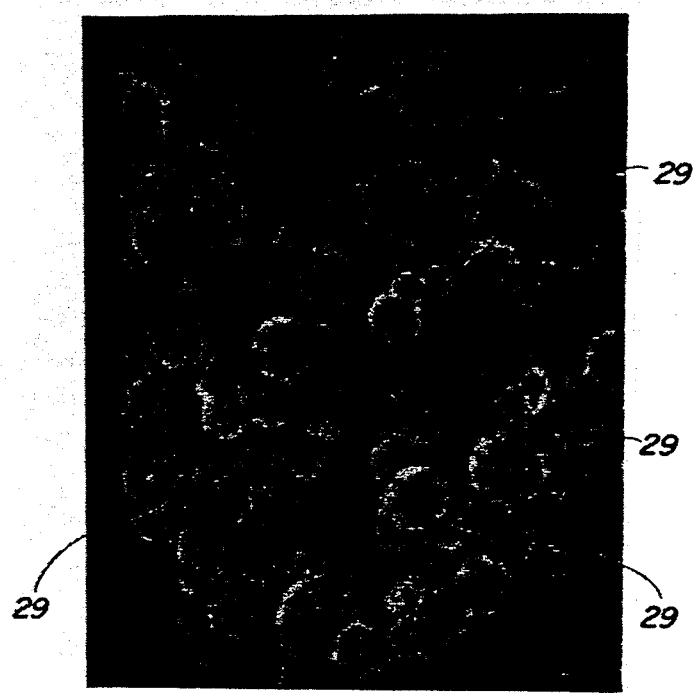
FIG. 5b is a photograph similar to that of FIG. 3b but magnified by an even greater amount so as to illustrate the plurality of the generally spherically-shaped particles which comprise a globule.

FIG. 5b is a photograph showing the generally spherically-shaped particles 29, which form the globules 28 as just noted. As observed in FIG. 5b, the particles 29 (only four of such are labeled) are somewhat randomly positioned after sintering, which gives rise to the desired somewhat irregular globule structure.

Figure 6:
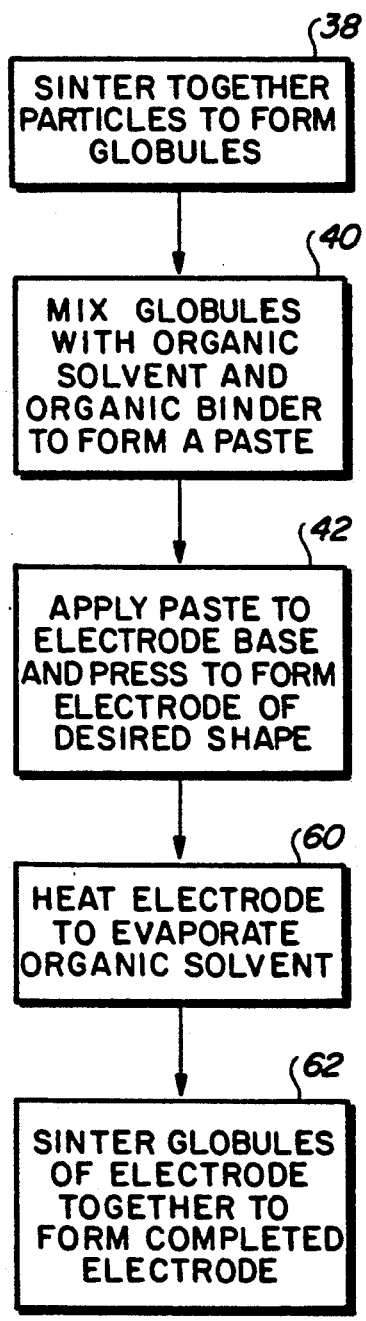
FIG. 6 is a block diagram illustrating the successive steps in a preferred method of making a porous electrode in accordance with the invention.

FIG. 6 depicts the successive steps in a preferred method of making the porous tip 20. In a first such step 38, small particles are joined together such as by sintering to form the globules 28, as previously described. This provides the globules 28 with a total surface area substantially greater than the surface area of spheres of similar size having smooth outer surfaces.

In a second step 40 of the method of FIG. 6, the globules 28 formed by the first step 38 are mixed with an organic solvent and an organic binder to form a paste. The solvent can be any appropriate organic solvent, with one example being diethylene glycol monohexyl ether sold under the trademark "CARBITOL" by Union Carbide Corporation of Danbury, Conn. The binder can be any appropriate organic binder such as the product sold under the trademark "EHEC HIGH" by Hercules Incorporated of Wilmington, Del. Initially a solution is formed consisting of four parts by weight of CARBITOL solvent to one part by weight of EHEC HIGH binder. The solution is then mixed with the globules 28 and additional CARBITOL solvent at the rate by weight of 20 percent solution, 60 percent globules and 20 percent CARBITOL solvent, to form a paste.

Figure 7:
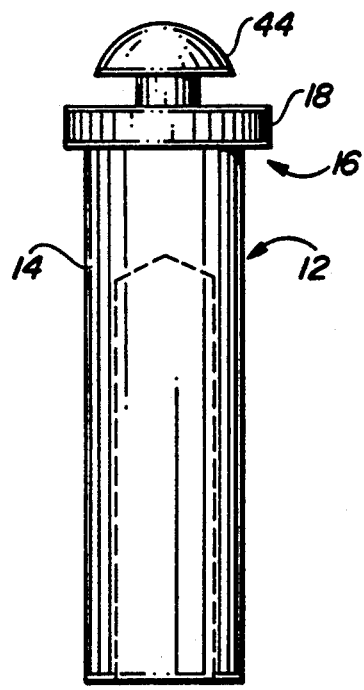
FIG. 7 is a plan view of an electrode stem used in the method of FIG. 6.

In a third step 42 of the method shown in FIG. 6, the paste formed in the second step 40 is applied to the electrode base 16 of the electrode stem 12 which is shown in detail in FIG. 7. As shown in FIG. 7, the electrode stem 12 includes a stud 44 which is of generally hemispherical configuration and which extends outwardly from the disc 18 at the end of the cylindrical body 14. The paste is applied to the stud 44 so as to surround the outside of the stud 44 including the space between the underside of the stud 44 and the disc 18. The paste as so applied is pressed so as to form the paste into the desired hemispherical shape.

Figure 8:
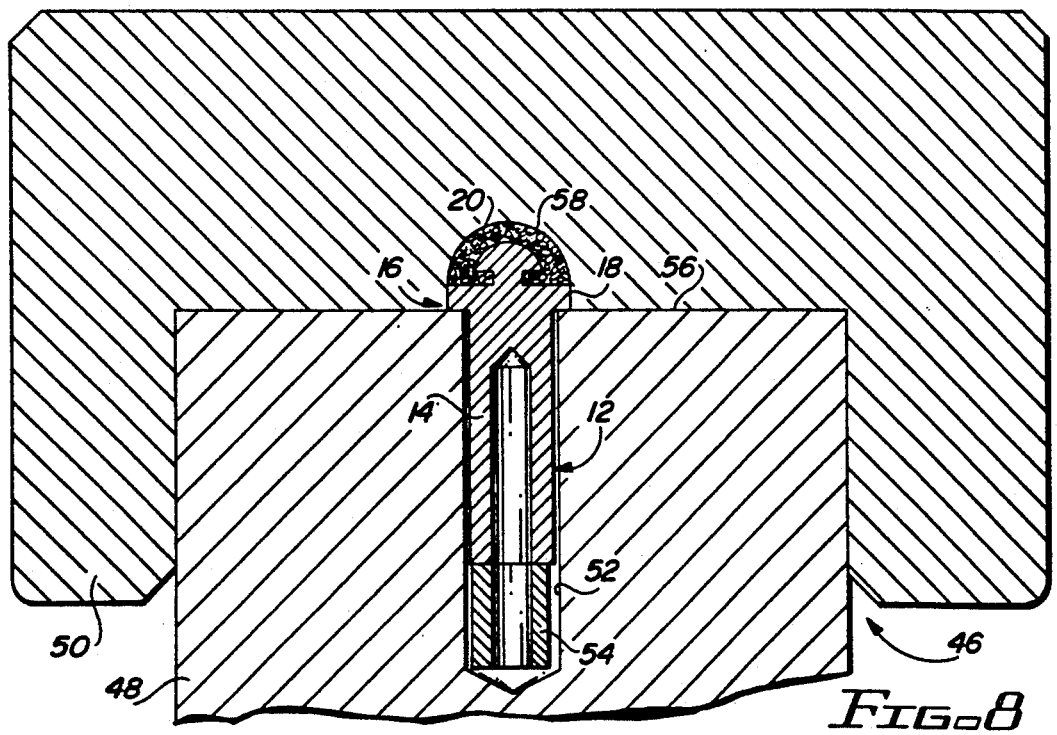
FIG. 8 is a sectional view of the holder and mating cap of a mold used to form a paste of platinum globules into a desired hemispherical shape at an electrode base at an end of the electrode stem of FIG. 7.

Pressing of the paste on the stud 44 is accomplished by a mold 46 which is shown in FIG. 8 and which includes a holder 48 and a mating cap 50. The holder 48 is of generally cylindrical configuration and has a central aperture 52, also of generally cylindrical configuration, formed therein. A silicone tube 54 is placed in the bottom of the aperture 52, and the electrode stem 12 is placed on top of the silicone tube 54. The disc 18 at the electrode base 16 of the cylindrical body 14 of the electrode stem 12 extends outwardly from the top of the aperture 52 so as to engage an upper surface 56 of the holder 48 when the electrode stem 12 is pressed into the aperture 52 by application of the cap 50 on the holder 48. The silicone tube 54 at the base of the electrode stem 12 acts to provide resiliency in connection with such action.

The cap 50 has a generally hemispherical cavity 58 at the underside thereof. As the cap 50 is placed over the holder 48 and forced downwardly, the hemispherical cavity 58 therein receives the paste which has been applied to the stud 44. As the cap 50 is forced toward the holder 48, the hemispherical cavity 58 forms the paste into a desired hemispherical configuration at the electrode base 16 of the electrode 10. The cap 50 is then withdrawn from the holder 48 and the electrode 10 is removed from the holder 48.

In a fourth step 60 shown in FIG. 6, the electrode 10 is placed in an oven where it is heated in order to evaporate the organic solvent from the paste. This forms the paste into a hardened, solidified mass in preparation for the final step of sintering.

In a fifth and final step 62 shown in the method of FIG. 6, the electrode 10 is placed in a sintering furnace where it is heated to a temperature just above the melting point of the globules. This results in the sintering together of the globules as well as sintering of such globules to the surfaces of the stud 44 and the disc 18 of the electrode stem 12. The binder evaporates during the sintering process, resulting in an electrode 10 which is made entirely of platinum.

While the invention has been particularly shown and described with reference to preferred embodiments thereof, it will be understood by those skilled in the art that various changes in form and details may be made therein without departing from the spirit and scope of the invention. For example, although a hemispherical electrode tip is described, it is to be understood that full spherical or parts thereof, as well as other shapes, such as parabolic, elliptical and the like, are also contemplated by the invention.

What is claimed is:

1. A method of making a porous electrode comprising the steps of:
    mixing a plurality of globules which are formed of a sintered material with a solvent and a binder to form a paste;
    applying the paste to an electrode stem;
    forming the paste into a desired shape; and
    sintering to bind the particles together.

2. The invention set forth in claim 1, wherein the globules are formed of platinum, the solvent comprises an organic solvent and the binder comprises an organic binder.

3. The invention set forth in claim 2, comprising the further step of heating the paste after it has been formed into a desired shape to evaporate the solvent prior to sintering.

4. The invention set forth in claim 3, wherein the step of forming the paste into a desired shape comprises the steps of placing the electrode stem with paste applied thereto in a mold having a cavity therein and pressing the cavity over the paste to form the paste into a desired shape.

5. The invention set forth in claim 4, wherein the stem has a generally cylindrical body with an electrode base at an end thereof, the step of applying the paste comprises applying the paste to the electrode base of the stem, and the mold comprises a holder having an aperture therein in which the electrode stem with paste applied thereto is placed and a cap having a generally hemispherical cavity therein, the cap being pressed onto the holder so that the cavity therein forms the paste into a generally hemispherical shape at the electrode base of the stem.

6. A method of making a porous electrode comprising the steps of:
    forming a plurality of globules having irregular surfaces of relatively high surface area, each of the globules being formed by sintering together a plurality of particles of substantially generally spherically-shaped particles of smaller size;
    applying the plurality of globules to an electrode base; and
    joining together the plurality of globules on the electrode base to form the porous electrode.

7. The invention set forth in claim 6, wherein each of the globules is formed by sintering together a plurality of the particles having diameters substantially less than the diameter of the globule.

8. The invention set forth in claim 7, wherein the step of joining together the plurality of particles comprises sintering together such particles.

* * * * *